United States Patent [19]

Sprenger

[11] Patent Number: 5,305,632
[45] Date of Patent: Apr. 26, 1994

[54] METHOD AND APPARATUS FOR MEASURING INTERFACIAL TENSION OF A LIQUID USING THE CAPILLARY RISE METHOD

[75] Inventor: Gregory S. Sprenger, San Jose, Calif.

[73] Assignee: Velcon Filters, Incorporated, San Jose, Calif.

[21] Appl. No.: 21,880

[22] Filed: Feb. 24, 1993

[51] Int. Cl.⁵ .................................... G01N 13/02
[52] U.S. Cl. .................................... 73/64.48
[58] Field of Search ....................... 73/64.48, 64.51

[56] References Cited

U.S. PATENT DOCUMENTS

| | | | |
|---|---|---|---|
| 2,401,053 | 5/1946 | Cupples | 73/64.51 |
| 3,048,999 | 8/1962 | Pochan | 73/64.48 |
| 3,881,344 | 5/1975 | Jobe | 73/64.51 |

FOREIGN PATENT DOCUMENTS

| | | | |
|---|---|---|---|
| 1060754 | 9/1986 | U.S.S.R. | 73/64.51 |
| 1571468 | 6/1990 | U.S.S.R. | 73/64.48 |
| 642962 | 9/1950 | United Kingdom | 73/64.48 |

*Primary Examiner*—Hezron E. Williams
*Assistant Examiner*—Joseph W. Roskos
*Attorney, Agent, or Firm*—Marshall & Melhorn

[57] ABSTRACT

A method and apparatus for determining the presence of surfactants in a liquid, such as a jet fuel or diesel fuel, by using the capillary rise technique, wherein an enclosed evacuated space is provided which is partially filled with water. A capillary tube is provided in the enclosed evacuated space having one of its ends submerged in the water. The liquid whose interfacial tension is to be measured is introduced into the evacuated space and the amount of rise in the capillary tube is measured. From the amount of rise in the capillary tube, the interfacial tension can be calculated. A high interfacial tension generally indicates the absence of surfactants which can affect the operation of coalescing filters which are designed to remove water from jet or diesel fuel before use.

12 Claims, 2 Drawing Sheets

METHOD AND APPARATUS FOR MEASURING INTERFACIAL TENSION OF A LIQUID USING THE CAPILLARY RISE METHOD

BACKGROUND OF THE INVENTION

1. Field of the Invention

The present invention relates to measuring the interfacial tension of a hydrocarbon liquid. The amount of interfacial tension is generally related to the amount of surfactants in the liquid. The amount of surfactants may affect the coalescing operation used to remove water from the liquid.

2. Description of the Prior Art

The necessity of removing water from fuels, such as JP4 or JP5 jet fuel, and the attendant dangerous icing conditions at high altitudes, is obvious. Water in diesel fuel can also be destructive to diesel engines during normal operations over a wide variety of operating temperatures.

It has been common to pass liquids, such as jet fuel or diesel fuel, through a coalescing operation using a coalescing filter at various times before use, such as during transfer from an underground storage tank to a tanker truck. Sometimes a coalescing filter is provided at the nozzle of the hose from the tanker truck to filter the fuel immediately before delivery into the fuel tank of the aircraft.

Presence of surfactants in the fuel being treated adversely affects the efficiency of the known filter coalescing elements and may render the element unable to remove the desired water content to produce clean dry fuel.

Accordingly, those experienced in the prior art have continually searched for a quick and easy way to determine the presence of surfactants in liquids.

SUMMARY OF THE INVENTION

The present invention relates to a method and apparatus for determining the presence of surfactants in a liquid by using the capillary rise technique. An enclosed evacuated space is provided which is partially filled with water. A capillary tube is provided in the enclosed evacuated space having one of its ends submerged in the water. The liquid whose interfacial tension is to be measured is introduced into the evacuated space. The amount of rise in the capillary tube is measured. From the amount of rise in the capillary tube, the interfacial tension can be calculated. A high interfacial tension generally indicates the absence of surfactants which can affect the operation of coalescing filters which are designed to remove water from jet or diesel fuel before use.

In one embodiment of the invention, a method is disclosed whereby the measurement of interfacial tension of a liquid is performed by providing an evacuated space partially filled with water, providing a capillary tube in the evacuated space having one of its ends in the water, introducing a liquid to be tested into the evacuated space, and measuring the rise of the water in the capillary tube.

In a further embodiment of the invention, a method is disclosed whereby the measurement of interfacial tension of a liquid is performed by providing an evacuated space partially filled with water, providing a capillary tube in the evacuated space having one of its ends in the said water, introducing a liquid to be tested into the evacuated space and measuring the rise of the water in the capillary tube, and calculating the interfacial tension according to a known formula.

In another embodiment of the invention, an apparatus is provided for practice of the aforementioned method. An evacuated glass tube is provided having an enclosing end wall at one end thereof, and a closure means at the other end thereof. A supply of water is provided therein. Also provided is a capillary tube having one of its ends in the supply of water, and a means for introducing a fuel sample into the evacuated space. Indicia is provided on the glass tube for directly reading the interfacial tension of the liquid.

A further object of the present invention is to determine the presence of surfactants in a hydrocarbon liquid.

A further object of the present invention is to determine the amount of surfactant in a hydrocarbon liquid by measuring the interfacial tension of the liquid.

A still further object of the present invention is to provide an apparatus for measuring the interfacial tension of a hydrocarbon liquid using the capillary rise technique.

A further object of the present invention is to provide an apparatus for measuring interfacial tension, including an evacuated test tube having a closure means and a predetermined amount of water therein, a capillary tube within said evacuated tube having one of its ends emersed in water, and indicia on the face of the evacuated tube which is used to read the interfacial tension by aligning the indicia with the fuel-water interface in the capillary tube.

Further objects and advantages of this invention will be apparent from the following description and appended claims, reference being made to the accompanying drawings forming a part of the specification, wherein like reference characters designate corresponding parts in the several views.

It is to be understood that the present invention is not limited in its application to the details of construction and arrangement of parts illustrated in the accompanying drawings, since the invention is capable of other embodiments, and of being practiced or carried out in various ways within the scope of the claims. Also, it is to be understood that the phraseology and terminology employed herein is for the purpose of description, and not of limitation.

DESCRIPTION OF THE PREFERRED EMBODIMENTS

Separation of undissolved water from fuels using coalescence is very dependent on the properties of the fuel water interface. One of these important properties is the interfacial tension (IFT). IFT is a measure which generally indicates the presence of surfactants and the degree to which they will degrade the separation of water using the coalescing process. Previous research has shown that coalescence is dependent on a number of complex interfacial properties, but interfacial tension is usually the first indicator used.

Surfactants are present in fuels for a variety of reasons. In some cases, they are a byproduct of the refining process. They can also be added to the fuel as components of additives, which impart anti-static or lubricity properties. In any case, they adversely affect the separation of water by coalescence.

There are a variety of techniques to measure interfacial tension. The technique which has proved successful is the capillary rise method. This method has historically been used to measure surface tension but it is not known to have been used for interfacial tension measurement before.

Figure 1:
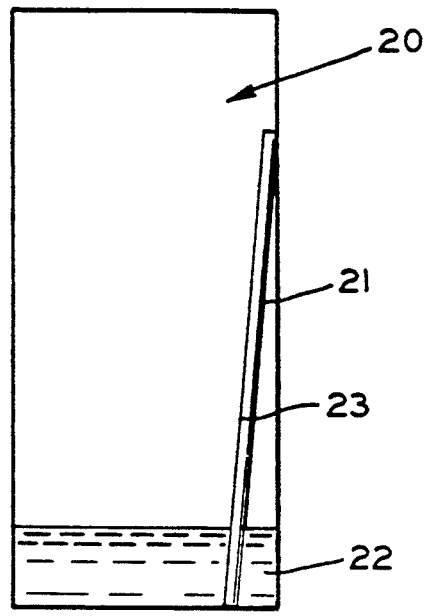
FIG. 1 is a diagrammatic view of an apparatus embodying the construction of the present invention.
Figure 2:
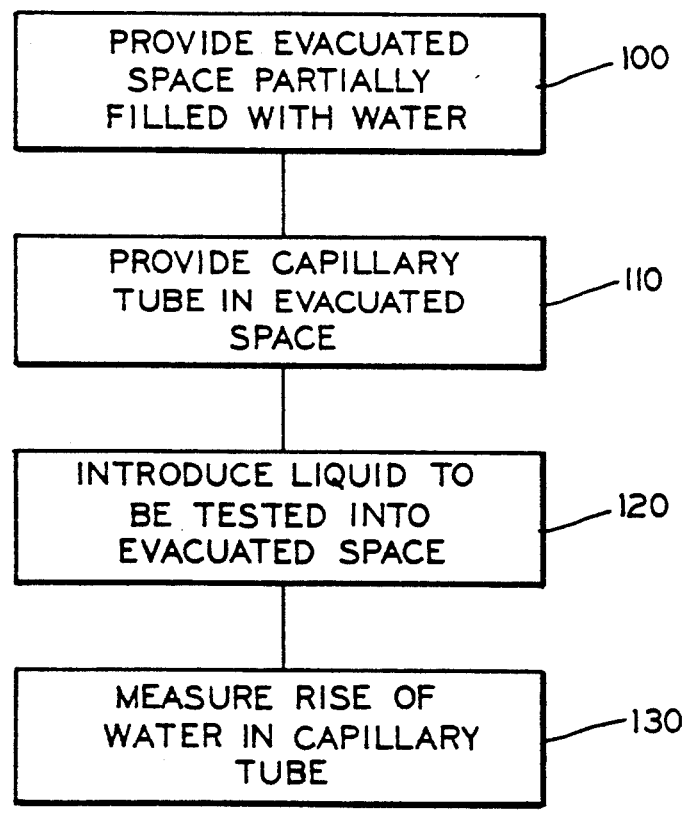
FIG. 2 is a chart showing a series of steps involved in the method of the present invention.
Figure 3:
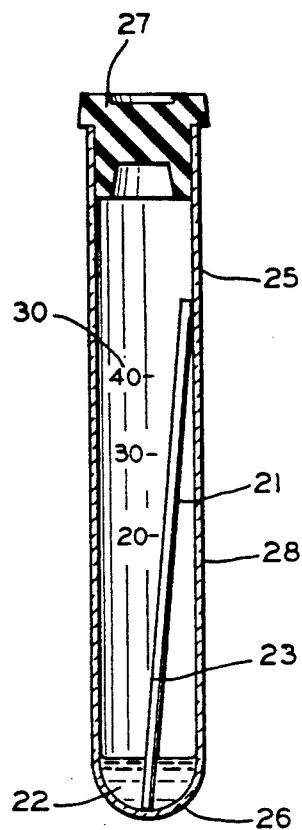
FIG. 3 is an elevational view of an apparatus embodying the construction of the present invention.

The capillary rise method theory was developed many years ago. The equation that describes the phenomena is:

$$\gamma = \frac{r \times \Delta\rho g h}{2 \times \cos\Theta}$$

where
  $\gamma$ = IFT, dynes/cm
  r = inner radius of capillary, cm
  $\Delta\rho$ = difference in liquid density, g/cm$^2$
  g = gravitational constant, 980 cm/sec$^2$
  h = rise of liquid in capillary, cm
  $\Theta$ = contact angle of water on capillary, degrees A diagrammatic view of an apparatus adapting the capillary rise technique to the measurement of interfacial tension is shown in FIG. 1. An enclosed evacuated space, generally indicated by the numeral 20, is provided. A capillary tube 21, preferably made of glass and of a diameter to be determined based on factors hereinafter described, is provided at the bottom of the evacuated space 20. For the practice of the capillary rise technique, there can be no bubbles or areas of separation in the capillary tube 21. Therefore, a supply of water 22 is provided at the bottom of the evacuated space 20. Because of the properties of the capillary tube 21, the water 22 will rise to the point indicated by the numeral 23 in the capillary tube 21.

Referring now to FIGS. 2-5, in the most preferred embodiment, the closed evacuated space is provided by a closed tube 25 having a formed or enclosing end wall 26 at one end thereof, and having the other end open. The tube may be made of any material which is strong enough to withstand the vacuum which needs to be introduced therein. A common tube which is used in the preferred embodiment is the readily available glass test tube 28. Indicia 30, indicating the amount of interfacial tension in a manner to be described, may be provided on the face of the test tube 28 if desired.

The measurement of interfacial tension is very sensitive to impurities and contamination. The test tube and the closure means must be carefully checked to avoid the possibility of such impurities and contamination. The greatest possibility of surfactant contamination exists with the rubber stopper. When the vacuum is introduced into the test tube 28, to insert the stopper 27 into the tube, a silicone is applied from a surfactant stabilized water solution. It was thought that a high probability existed that surfactant from the solution remained on the stopper after treatment. However, initial testing showed little, if any, surfactant remaining on the stopper. Interfacial tension measured using the capillary rise method matched those measurements using the ring method quite closely, showing that apparently silicone is deposited and the surfactant carrier stabilizer is not. However, depending upon the particular stopper or closure means 27 which is used, the possibility of contamination should be checked.

Another concern is the effect of fuel and water temperature. It has been found that surface tension is inversely proportional to the temperature of the liquid sample. When sample temperature rises, surface tension falls. It can be assumed that IFT will behave similarly. Tests have shown that the change in surface tension with temperature (d$\gamma$/dT) for both light hydrocarbons and water is approximately equal to $-0.10$ dynes/cm/°C. This means that surface tension increases approximately equal to 2.5 dynes/cm going from 70° F. to 32° F., and falls approximately equal to 2.0 dynes/cm at 100° F. This is coextensive with the usable range in the field. It is thought that IFT d$\gamma$/dT is similar. Therefore, any effect of fuel and water temperature would not be significant enough to warrant correction. However, depending on the particular liquid being tested, this factor may need to be taken into account.

For proper IFT measurement, the capillary tube 21 must be filled with a liquid, such as water 22, with no air pockets. In addition, the water 22 must be continuous in the capillary tube 21 from the bottom up, and the liquid or fuel to be introduced from the top of the capillary tube 21 down. If pockets of fuel or water 21 are contained in the other, a false reading will result. This makes fuel entry into the tube important.

It is best for the capillary tube 21 to be wetted by the water 22 before fuel enters the tube. This guarantees a "receding" interface between the fuel and the water 22, which improves the wetting of the capillary walls with the water 22, resulting in better readings.

Figure 4:
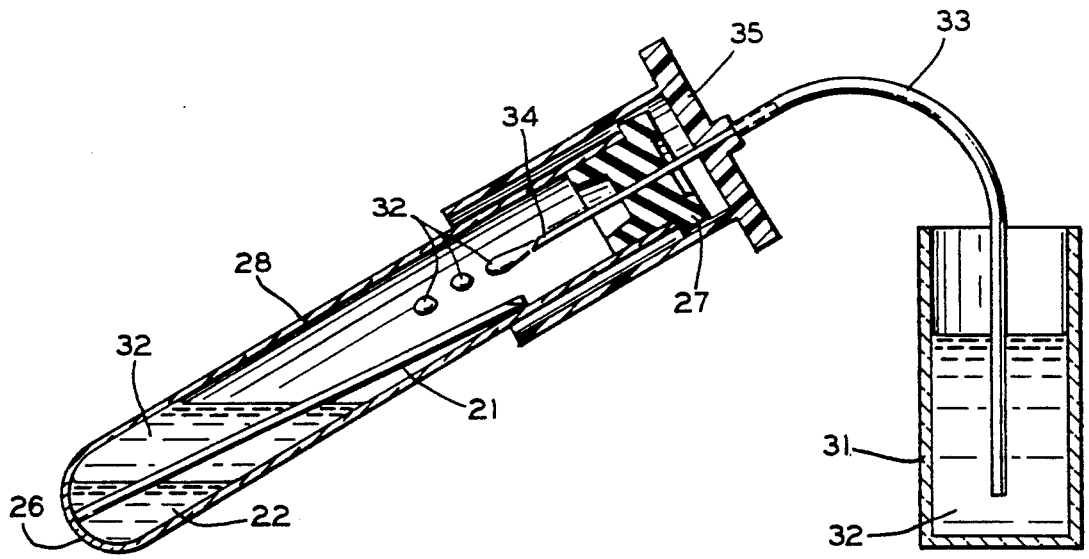
FIG. 4 is a diagrammatic elevational view which shows filling the apparatus of FIG. 3 with the liquid to be tested.

Referring to FIG. 4, the best way to accomplish these requirements is to tilt the tube 28 to approximately 30° from the horizontal. This keeps the water 22 at the bottom 26 with the capillary tube 21 submerged. In addition, because of the tilting and the factor "$\Delta\rho g h$" in the equation, the water 22 will travel up the capillary tube 21 to near the top, eliminating air bubbles and ensuring a receding interface.

A container 31 holds the liquid to be tested or fuel sample 32. A tubing 33 connected to a hollow needle 34, held by a needle holder 35, is provided. With the tubing 33 held in the fuel sample 32, the needle 34 is made to puncture the stopper 27 and be in fluid communication with the vacuum inside the test tube 28. The vacuum inside the test tube 28 draws the fuel sample 32 into the test tube. The vacuum provided in the test tube 28 is sufficient to draw in enough fuel to substantially fill the test tube 28. It can be understood that the larger the test tube, the more vacuum must be introduced.

The fuel 32 initially displaces some water in the capillary tube 21, pushing the existing water out of the tube, and keeping it full. After the predetermined amount of fuel 32 is drawn into the test tube 28, the needle 34 is removed from the stopper 27. Because the opening made in the stopper is self-sealing, any further communication with atmosphere is eliminated. The test tube 28 is then returned to a vertical position and allowed to remain at rest for a period of time before reading.

Figure 5:
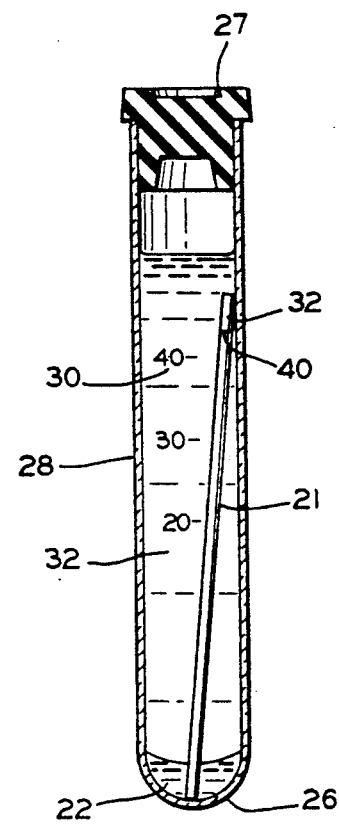
FIG. 5 is an elevational view of the apparatus shown in FIG. 3 after the liquid sample has been introduced, and the apparatus has been returned to a vertical position so that the rise of the water in the capillary tube may be measured.

After the test tube 28 sits for a few minutes, the fuel water interface 40 is aligned with the indicia 30 to find an indication of the interfacial tension. As shown in FIG. 5, in the particular example, IFT=43.

The particular test tube size, capillary tube size, and indicia will depend upon the application and the materials available. In a particular evacuated test tube and stopper combination manufactured by applicant's assignee, and sold under the name "Hydrokit®", the interior of the test tube available for use is approximately 70 mm in height. The capillary tube used in the interior of such test tube for jet fuel must be sufficient to read as high as 45 dynes/cm. For jet turbine fuel $\Delta \rho = 0.19$ g/cm$^3$, and the contact angle is 25° based on experimental measurements. This makes $\cos\Theta = 0.9$. Since part of the height of the capillary tube will be taken up by the water, and it is preferred that the capillary tube not impinge on the stopper, the usable length of the capillary tube in this example may be determined to be 55 mm. Using the aforementioned formula with the values given, the inside diameter of the capillary tube should be 1.4 mm, and the formula becomes:

$$\gamma = 7.24h$$

where
$\Theta = 25°$
$\cos\Theta = 0.90$
h = units of cm
$\gamma$ = units of dynes/cm This may now be used to calculate the IFT, and properly place the indicia 30 on the tube. If the use of a different size test tube is desired, the above formula may be used to calculate a different diameter or length of the capillary tube. These values, of course, will vary depending upon the liquid being measured and for each application, an optimum apparatus may be designed.

Thus, by carefully studying the problems present in measuring surfactants and utilizing the capillary rise method not previously used for this purpose, a novel method and apparatus is produced.

What is claimed is:

1. A method of measuring interfacial tension of a liquid using capillary rise, said method including the steps of:
   a) providing an enclosed evacuated space partially filled with water,
   b) providing a capillary tube within said evacuated space having one of its ends submerged in said water,
   c) introducing a supply of liquid whose interfacial tension is to be measured into said evacuated space, and
   d) determining the height of the water in said capillary tube.

2. The method defined in claim 1, and including the additional step of:
   a) calculating the interfacial tension of the liquid.

3. A method of determining the interfacial tension of a liquid, said method including the following steps:
   a) providing an evacuated tube having an end wall at one end and closed by a closure means at the other end and partially filled with water,
   b) providing a capillary tube in said evacuated tube having one end submerged in the water,
   c) tilting said evacuated tube to a 30° angle with the horizontal,
   d) introducing a quantity of liquid to be tested into said evacuated tube while said tube is tilted,
   e) returning said evacuated tube to a vertical position,
   f) letting said evacuated tube remain at rest for a predetermined time period, and
   g) measuring the rise of the water in said capillary tube as indicated by the position of a liquid/water interface in the capillary tube.

4. The method defined in claim 3, and including the additional step of:
   a) calculating the interfacial tension of the liquid using the rise of the water in said capillary tube.

5. The method defined in claim 3, and including the additional step of:
   a) providing indicia on said evacuated tube to provide for direct reading of the interfacial tension by aligning the position of the liquid/water interface with the indicia.

6. A interfacial testing apparatus including:
   a) a tube closed at one end and open at the other end;
   b) a capillary tube provided in said tube having one of its ends proximate the bottom of said tube;
   c) a predetermined quantity of water provided in said tube;
   d) a stopper closing the other end of said tube, said tube being evacuated after said stopper is placed therein; and
   e) means to introduce a sample of liquid to be tested into said tube.

7. The apparatus defined in claim 6, wherein said means to introduce includes:
   a) a needle holding means;
   b) a hollow needle centrally located in said needle holding means; and
   c) a length of tubing in fluid communication with said hollow needle.

8. The apparatus defined in claim 7, wherein said means to introduce further includes:
   a) a reservoir for holding the sample of liquid to be tested.

9. The apparatus defined in claim 8, wherein said needle holding means includes a skirt to partially enclose the top of said tube when said hollow needle is inserted.

10. The apparatus defined in claim 9, wherein said tube is glass.

11. The apparatus defined in claim 10, wherein said stopper is rubber.

12. The apparatus defined in claim 11, wherein said glass tube has placed thereon indicia for directly reading the value of interfacial tension.

* * * * *